(12) United States Patent
DeGrood

(10) Patent No.: US 7,552,646 B1
(45) Date of Patent: Jun. 30, 2009

(54) METHODS AND APPARATUS FOR WRINKLE RESISTANCE TESTING

(75) Inventor: Kevin Blase DeGrood, Livonia, MI (US)

(73) Assignee: Toyota Motor Engineering & Manufacturing North America, Inc., Ann Arbor, MI (US)

( * ) Notice: Subject to any disclaimer, the term of this patent is extended or adjusted under 35 U.S.C. 154(b) by 0 days.

(21) Appl. No.: 12/018,777

(22) Filed: Jan. 23, 2008

(51) Int. Cl.
*G01N 3/00* (2006.01)
(52) U.S. Cl. ........................................ 73/788
(58) Field of Classification Search ............... 73/788
See application file for complete search history.

(56) References Cited

U.S. PATENT DOCUMENTS

| | | | |
|---|---|---|---|
| 2,670,627 A | | 3/1954 | Shaw et al. |
| 3,620,071 A | * | 11/1971 | Kelley et al. ................... 73/847 |
| 5,396,804 A | * | 3/1995 | Moet et al. ..................... 73/788 |
| 6,112,589 A | * | 9/2000 | Tressler et al. ................. 73/160 |
| 6,332,364 B1 | * | 12/2001 | Buschmann et al. ........... 73/788 |
| 6,370,962 B1 | * | 4/2002 | Sullivan et al. ................ 73/826 |
| 6,609,408 B2 | | 8/2003 | Chen et al. |
| 6,647,802 B2 | * | 11/2003 | Willson-Hackworth et al. ............................ 73/826 |
| 7,013,705 B2 | * | 3/2006 | Wortmann et al. ............... 73/7 |
| 7,258,022 B2 | * | 8/2007 | Wenski ........................ 73/800 |
| 2006/0036410 A1 | | 2/2006 | Pan |

FOREIGN PATENT DOCUMENTS

WO   WO 2006/014870 A2   2/2006

* cited by examiner

*Primary Examiner*—Lisa M Caputo
*Assistant Examiner*—Octavia Davis
(74) *Attorney, Agent, or Firm*—Pramudji Wendt & Tran, LLP

(57) ABSTRACT

An apparatus for testing wrinkle resistance of a material, the apparatus including a base for receiving the material, the base coupled to a frame, at least one clamp for holding the material, the at least one clamp disposed upon the frame and movably fixed to an edge of the base and a loading mechanism for applying a desired load quantity on the material on the base. A method for testing wrinkle resistance of material, the method including providing a material on a base, the base coupled to a frame, providing at least one clamp for holding the material, the at least one clamp disposed upon the frame and movably fixed to an edge of the base and controlling a loading mechanism to apply a desired load quantity on the material on the base.

14 Claims, 5 Drawing Sheets

METHODS AND APPARATUS FOR WRINKLE RESISTANCE TESTING

BACKGROUND

1. Technical Field

The present disclosure relates generally to testing methods and apparatus. More specifically, but without limitation, the present disclosure relates to methods and apparatus for testing wrinkle resistance of materials used on vehicle seats.

2. Background Information

Seats for motor vehicles may include a structural frame, padding, and a cover. During the life of a vehicle such as an automobile, various forces may be exerted on the vehicle seat. For example, a passenger or driver may exert forces on the vehicle seat while sitting in a seat, getting in and out of a seat, or when a vehicle maneuvers. Since each passenger or driver may have a different size, weight, weight distribution, and shape, it is difficult to predict the variety of forces that may be exerted on the vehicle seat. Thus, vehicle manufacturers may perform testing on a vehicle seat to check for safety, durability, wrinkling, recoverability, comfort, feel, and the like.

In the early stages of a vehicle's development, a material may be selected for a seat cover before a seat design is determined. The material may be preliminarily tested and appear to be satisfactory for a seat cover. However in the latter stages, the material may fail full seat testing due to improper performance or an abnormality such as wrinkling. Changes to a fabric selection in the final stages of a vehicle's development may cause significant production delays, re-design of the seats, additional costs or other inefficiencies in the manufacturing process.

Thus a need remains for methods and apparatus for testing wrinkle resistance of materials to be used on vehicle seats prior to full seat testing.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

One aspect of the disclosure provides an apparatus for testing wrinkle resistance of a material, the apparatus including a base for receiving the material, the base coupled to a frame, at least one clamp for holding the material, the at least one clamp disposed upon the frame and movably fixed to an edge of the base and a loading mechanism for applying a desired load quantity on the material on the base.

Another aspect of the disclosure provides a method for testing wrinkle resistance of material, the method including providing a material on a base, the base coupled to a frame, providing at least one clamp for holding the material, the at least one clamp disposed upon the frame and movably fixed to an edge of the base and controlling a loading mechanism to apply a desired load quantity on the material on the base.

Yet another aspect of the disclosure provides a testing method by an apparatus for testing wrinkle resistance of a material including a base for receiving the material, the base coupled to a frame, at least one clamp for holding the material, the at least one clamp disposed upon the frame and movably fixed to an edge of the base and a loading mechanism for applying a desired load quantity on the material on the base.

BRIEF DESCRIPTION OF THE DRAWINGS

For detailed understanding of the present disclosure, references should be made to the following detailed description of the several aspects, taken in conjunction with the accompanying drawings, in which like elements have been given like numerals and wherein.

DETAILED DESCRIPTION

Figure 1:
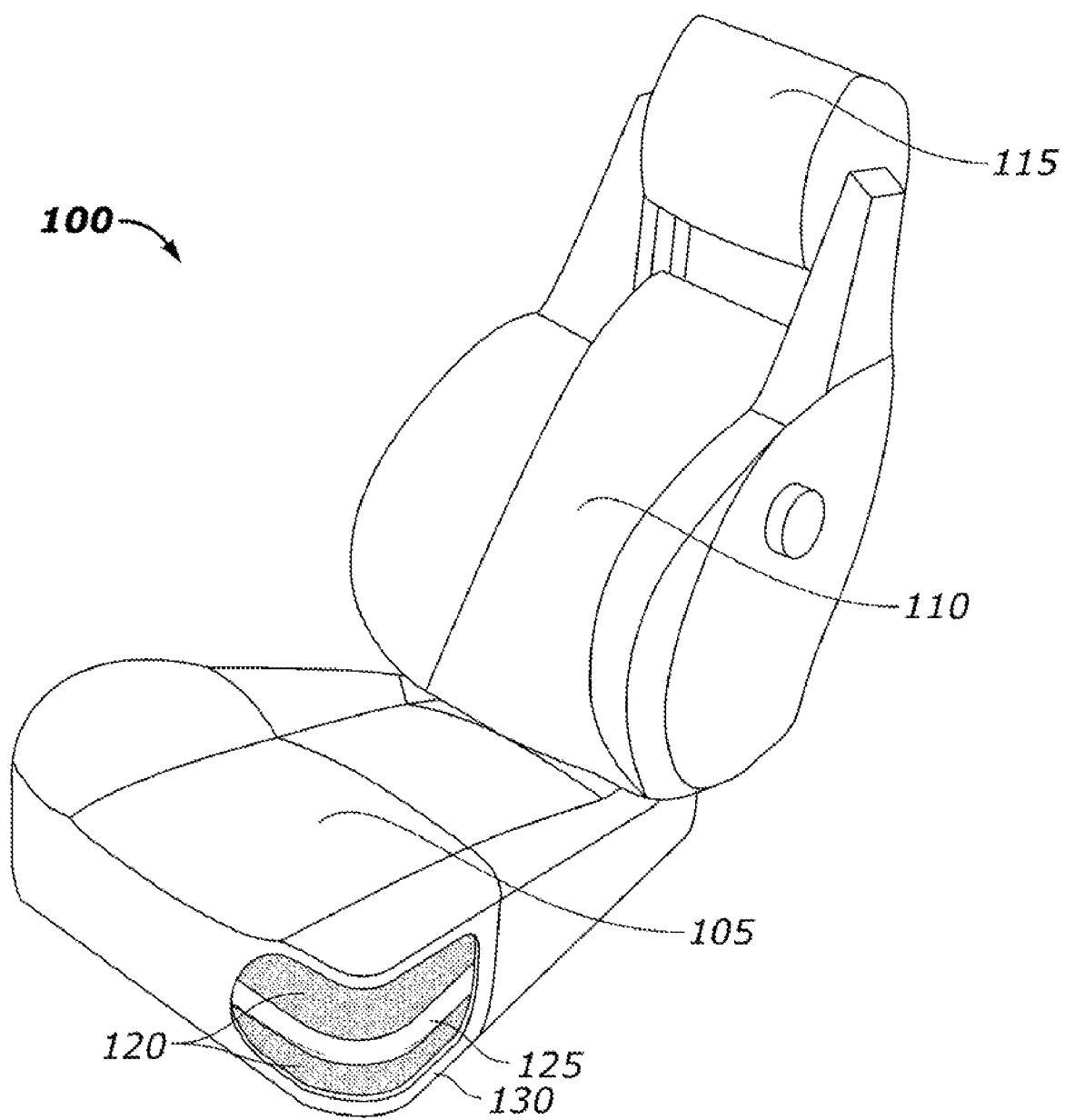
FIG. 1 represents a perspective view of an illustrative implementation of a vehicle seat including a cut-away portion of the seat.

Although the present disclosure has been described with reference to specific implementations, it will be understood by those skilled in the art that various changes may be made without departing from the spirit or scope of the invention. Various examples of such changes have been given in the forgoing description. Accordingly, implementations of the disclosure are intended to be merely illustrative of the scope of the invention and are not intended to be limiting. It is intended that the scope of the invention shall be limited only to the extent required by the appended claims. For example, to one of ordinary skill in the art, it will be readily apparent that vehicle seats as discussed herein may be implemented in a variety of implementations, and that the forgoing discussion of certain of these implementations does not necessarily represent a complete description of all possible implementations.

For simplicity and clarity of illustration, the drawing and/or figures illustrate the general manner of construction, and descriptions and details of well known features and techniques may be omitted to avoid unnecessarily obscuring the disclosure.

Referring to FIG. 1, an illustrative implementation of a vehicle seat is generally indicated at 100. As used herein, a vehicle seat may refer to any seating unit used by a driver or passenger in any vehicle or mode of transportation including but not limited to an automobile, truck or motorcycle. As shown, the vehicle seat 100 may include a seat surface 105, a seat back 110 and headrest 115. It should be understood that the present disclosure has applicability to vehicle seats as broadly described above, and is not intended to be limited to the vehicle seat 105 as specifically described.

The seat surface 105 may further include various elements such as a structural frame 125, padding 120, and a cover 130. A structural frame 110, constructed of any suitable material such as metal, may provide a general shape or structure for the vehicle seat 105. The padding 120 may be provided on either side of the structural frame 110 to provide comfort, shape, and/or support. Foam, a synthetic fill, or any other conventional material may be used as the padding 120. A cover 130 may be placed over the structural frame 110 and the padding 120. A cover 130 may be used to hold the padding 120 in place around the structural frame 110. As utilized herein, a cover 130 may utilize a material or fabric such as cotton, polyester, vinyl, leather, suede, and/or any other suitable material. In one possible implementation, a cover 130 may utilize one of the materials previously listed bonded to a thin layer of padding.

Figure 2:
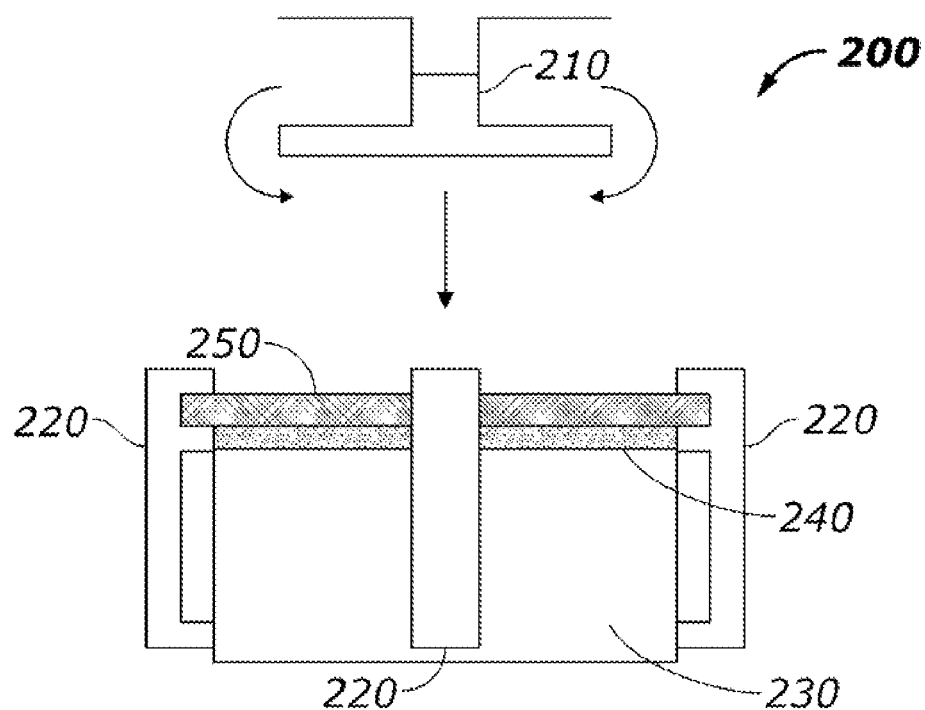
FIG. 2 represents a side view of an illustrative implementation of an apparatus for testing vehicle seat materials.

Referring now to FIG. 2, an illustrative implementation of an apparatus for testing vehicle seat materials is generally indicated at 200. The apparatus 200, which may be used to simulate a variety of forces that may be exerted on a seat surface 105 during its lifetime, may include a base 230, at least one clamp 220 and a loading mechanism 210. Resulting data provided by the apparatus 200 may allow improved prediction of how a material may perform as a seat cover 130. The apparatus 200 may also provide data indicating durability, how much a material stretches the ability for a material to recover to its original shape, and the like. Further, the apparatus 200 may be utilized to determine the response of the material 250 to induced wrinkling by the loading mechanism (to be described below).

A base 230 may be constructed of steel, aluminum, or any other suitable material that may withstand the applied pressure and loads from the loading mechanism (to be described below). As shown in FIG. 2, the base 230 may be of a cylindrical shape with a substantially circular surface to receive a type of material 250. Also shown between the base 230 and the material 250 is a layer of padding 240 which may be the same type of padding to be used in the vehicle seat 100 or the like, in order to more accurately simulate an expected configuration of a seat surface 105. At least one clamp 220 (to be described below) may be secured to the edge of the base 230 and utilized to secure a material 250 for testing.

The base 230 may be coupled to a loading mechanism 210 via a frame (described below) which provides structure to the apparatus 200. The loading mechanism 210 comprising a pressure head or load cell may apply a load to a material 250 on a base 230. The loading mechanism 210 may be constructed of a metal, plastic, rubber, some combination thereof, or any other suitable material. As a source of power, the loading mechanism 210 may utilize a hydraulic system, an electric system, or the like to apply a constant force on a material 250. While it is shown in FIG. 2 that the bottom portion of the loading mechanism 210 appears to be a flat surface, in other illustrative implementations, the bottom portion of the loading mechanism 210 may be rounded or grooved and it may also have contours, a rubber cover, or the like to improve grip on a material 250. A loading mechanism 210 may also be implemented using a substantially circular surface, however, any shaped-surface may be utilized that would allow an equal amount of force to be exerted on a material 250 in all directions. In one implementation, a loading mechanism 210 may rotate while applying a constant load to cause twisting, wrinkling or stretching of the material 250. Furthermore, the loading mechanism 210 may vibrate or move in a gyrating motion concurrently while rotating to cause twisting, wrinkling or stretching of the material 250.

The loading mechanism 210 may apply any desired load quantity as determined by an operator. By way of example, a desired load quantity may be a predetermined target, as designated by an operator, in the range of about 1 kg to about 10 kg. In another example, a desired load quantity may be at least 10 kg.

Continuing with FIG. 2, several clamps 220 are shown which may secure a material 250 at a substantially constant tension onto a base 230. As shown, a clamp 220 may appear as a substantially rectangular fastening piece coupled perpendicularly to the base 230. The clamps 220 securing a material 250 may move in response to the twisting, wrinkling or stretching of the material 250 in which case the movement of the clamps causes the material 250 to be fixed at a substantially constant tension. By way of example, a strain gauge (to be described below) may be utilized to detect the tension in a material 250 and adjustments to a clamp 220 may be made accordingly.

Several clamps 220 may be fixed to an edge of a base 240 so that distance moved by each clamp 220 may be measured in several directions. In addition to providing a distance that each clamp 220 has moved, data regarding the direction of the movement by each clamp 220 may also be provided. Further, the distance each clamp 220 moves may be compiled and averaged to provide a general indication of the wrinkle resistance of a material. Further, the time needed for a material 250 to recover to its original shape may also be recorded and provided. By measuring these properties, a material 250 can be evaluated prior to testing a fully assembled seat for durability, wrinkling, stretching, recovery, or the like.

By way of example only, output produced by the apparatus 200 may be in the form of the distance in millimeters (mm) that the material 250 stretches in each of the 8 cardinal directions. Following the accumulation of data regarding the stretching of material 250, the data may be compared to or correlated with other factors including, but not limited to, seat application, type of seating material, lamination thickness, full seat evaluation results, and field issues. Such data may help predict the outcome of full seat evaluation based on trends with material type, foam lamination thickness, and seat applications.

Figure 3:
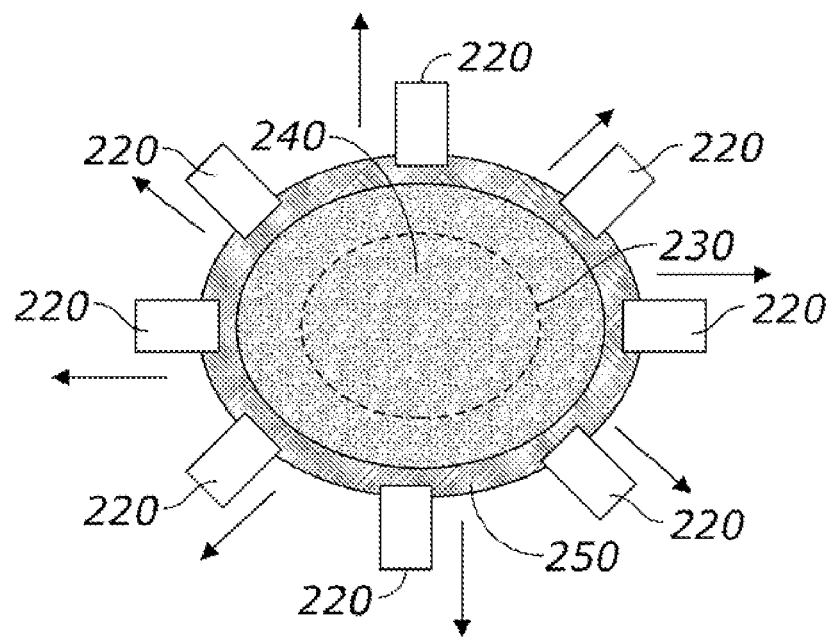
FIG. 3 represents a top view of the apparatus of FIG. 2.

Referring now to FIG. 3, an overhead view of an apparatus 200 for testing vehicle seat materials is provided. The overhead view provides a view of a base 230, clamps 220, material 250, and padding 240. A loading mechanism 210 seen shown in FIG. 2 has not been shown to allow the other components of the device to be clearly visible. A layer of padding 240 may be placed on top of a base 230, and a material 250 may be placed on top of the padding 240 for testing. As shown, a material 250 may be larger than a base 230 to allow several clamps 220 to secure the material for testing. While in the implementation shown, eight clamps 220 are provided, any suitable number of clamps may be utilized. As discussed previously, a loading mechanism (not shown) may be lowered onto the material 250 and padding 240 on a base 230 to apply a constant load.

Figure 4:
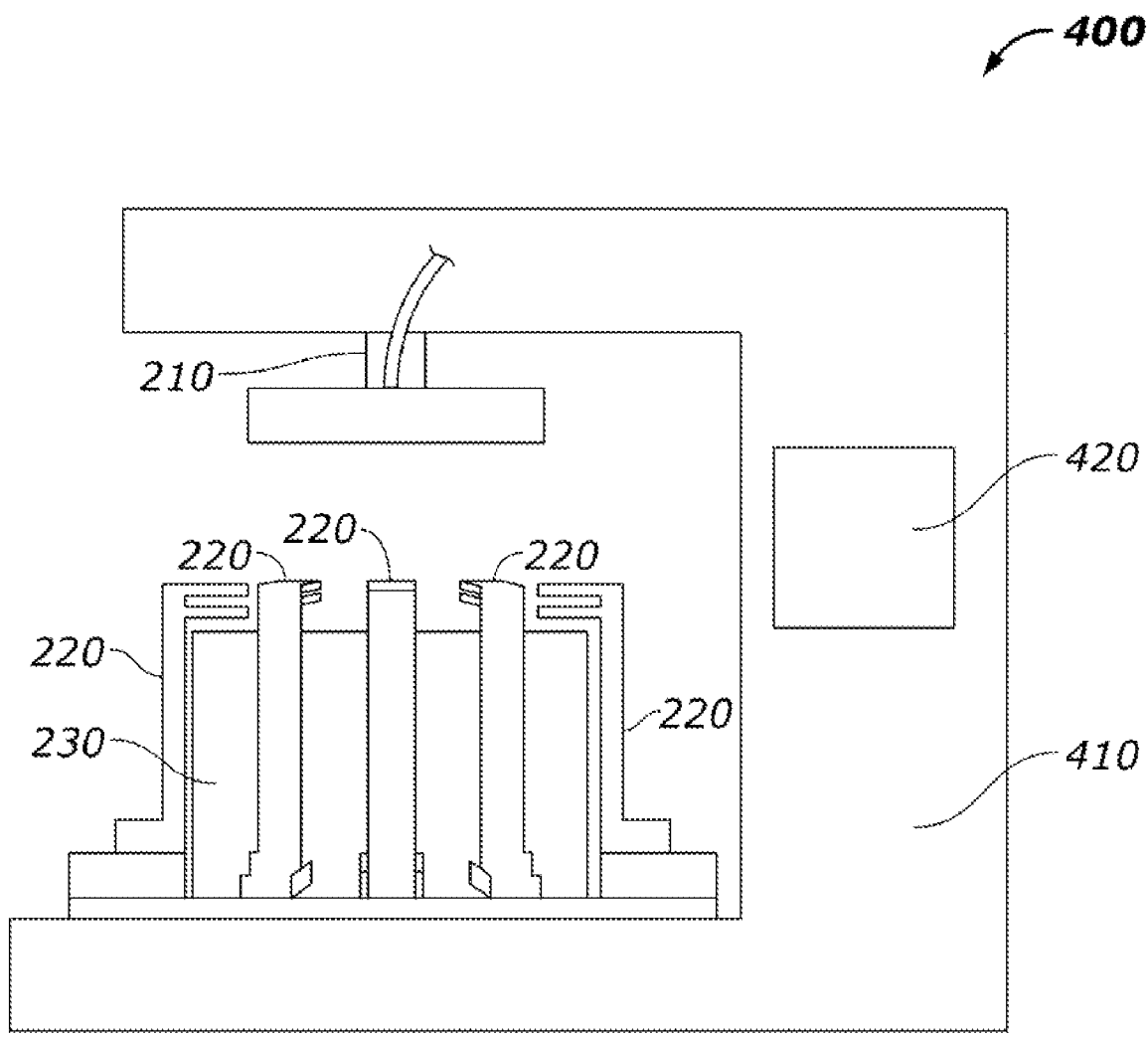
FIG. 4 represents a side view of the apparatus of FIG. 2.

FIG. 4 provides a side view of an apparatus 200 for testing vehicle seat materials. As described herein, the apparatus 200 may include a base 230 coupled to at least one clamp 220 with one end for receiving a material (not shown) for wrinkle resistance testing. A second end of each clamp 220 may be mounted upon a frame 410 which may also be coupled to the loading mechanism 210 for applying a load to the material atop the base 230. As shown, the frame 410 may be formed in a substantially rectangular shape and constructed of any suitable firm material such as, but not limited to, metal. Affixed to a surface of the frame 410 is shown a control board 420. The control board may provide switches and settings (not shown) to allow an operator to control the load applied or movement made by the loading mechanism 210.

Figure 5:
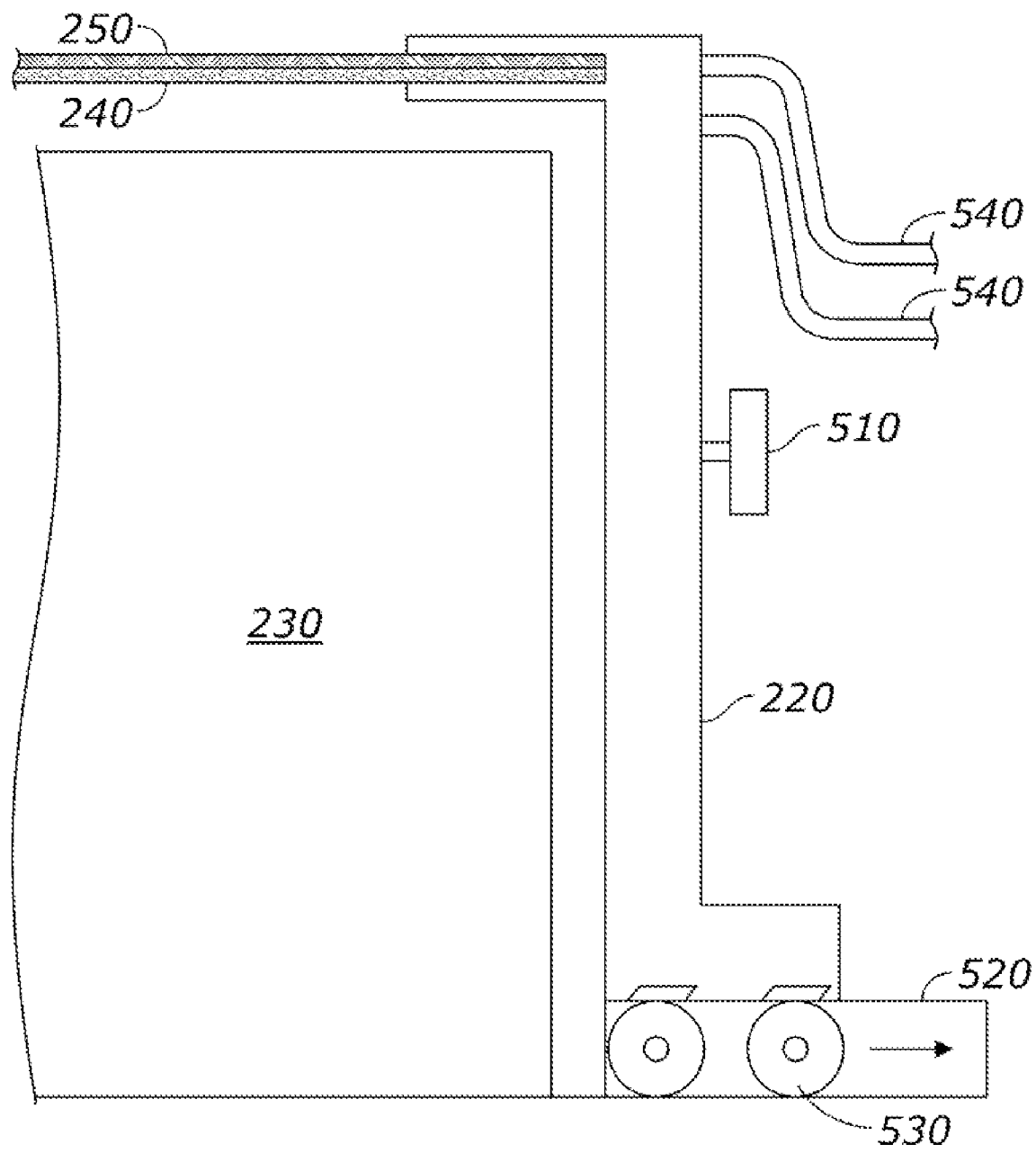
FIG. 5 represents a fragmentary side view of a clamp of the apparatus of FIG. 2.

Referring now to FIG. 5, a side view of an illustrative implementation of a clamp 220 is provided. As discussed previously, a clamp 220 may fix a material 250 and padding 240 atop base 230 at a substantially constant tension while a pressure head 210 applies a load on the material 250 and padding 240. A clamp 220 may secure a material 250 utilizing a spring actuated mechanism, a fastener, or the like. For example, in one implementation, a fastener 510 may be rotated to cause a clamp 220 to tighten and secure a material 250. Each clamp 220 may mounted on a separate track 520 that allows a clamp 220 to move back and forth. One or more wheels 530 may be coupled to a clamp 220, the wheels 430 sliding along a track 520. Movement along a track 520 may be driven by a belt, a chain, a rack and pinion, or the tike. By way of example, the wheels 530 may be coupled to a chain that may cause the wheels 530 to rotate along a track 530. A clamp 220 may also include a strain gauge (not shown) or the like to measure the tension of a material 250. Leads 540 from a strain gauge may provide a signal indicating the tension of a material 250 to a controller. In accordance with signals from the strain gauge, a clamp 220 may be adjusted to maintain a constant tension in the material 250. Each track 520 may also be coupled to a distance sensor (not shown) so that a distance moved by each clamp 220 during testing may be measured and provided to an operator. In addition, an average distance moved by the clamps may also be calculated following the accumulation of distances moved by the clamps 200. Scaled values which correlate results from wrinkle resistance testing to results from full seat testing may be provided as well.

Figure 6:
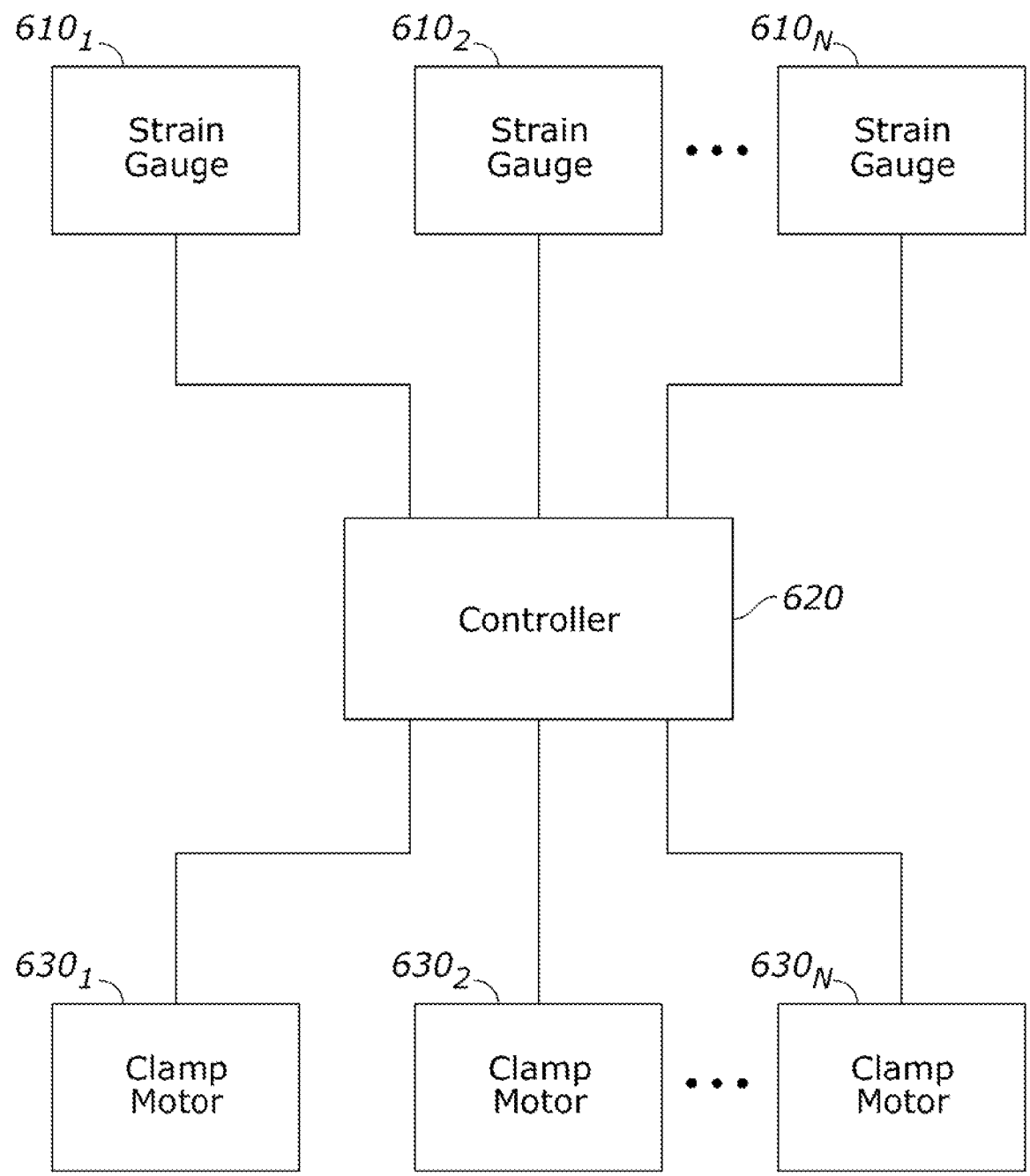
FIG. 6 represents an illustrative implementation of a clamp control mechanism.

FIG. 6 provides an illustrative implementation of a clamp control device. Each clamp 220 in an apparatus 200 for wrinkle resistance testing may have a corresponding strain gauge $610_1$, $610_2$, $610_N$ to detect the tension at which a material 250 is being held. Each strain gauge 610 may provide the detected tension to a controller 620. Based on values received from each strain gauge 610, a controller 620 may adjust one or more clamps to maintain a constant tension on a material. A controller 620 may provide a signal to one or more clamp motors $630_1$, $630_2$, $630_N$ to cause one or more clamps 220 to adjust as needed to keep the material at a constant tension.

The various implementations of the present disclosure may allow a material to be tested prior to full seat testing. Statistical data regarding a material's durability, ability to stretch, ability to recover after repeated stretching, resistance to abrasion, resistance to tearing and the like may be gathered and/or predicted utilizing the methods and apparatus described herein. By providing a more accurate simulation of the dynamic forces that may be applied to a material as part of a vehicle seat, a material that is more likely to pass full seat testing, thus avoiding delays in production and development.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein and/or use of equivalent functional junctions for couplings/links described herein.

What is claimed is:

1. An apparatus for testing wrinkle resistance of a material, the apparatus comprising:
    a base for receiving the material, the base coupled to a frame;
    at least one clamp for holding the material, the at least one clamp disposed upon the frame and movably fixed to an edge of the base, wherein the at least one clamp is coupled to a track allowing the at least one clamp to be movable with the material on the base;
    a loading mechanism for applying a desired load quantity on the material on the base; and
    a distance sensor to test the wrinkle resistance of the material, wherein the distance sensor is coupled to the track operable to record movement of the at least one clamp in multiple directions.

2. The apparatus of claim 1, wherein the loading mechanism comprises a pressure head for applying a constant load quantity to the material.

3. The apparatus of claim 1, wherein the loading mechanism rotates while applying a desired load quantity on the material on the base.

4. The apparatus of claim 1, wherein the loading mechanism is controlled such that the desired load quantity is a predetermined target value.

5. The apparatus of claim 4, wherein the predetermined target value is from about 1 kilograms (kg) to about 10 kg.

6. The apparatus of claim 1 further comprising at least one strain gauge coupled to the at least one clamp to hold the material at a constant tension.

7. A method for testing wrinkle resistance of material, the method comprising:
    providing a material on a base, the base coupled to a frame;
    providing at least one clamp for holding the material, the at least one clamp disposed upon the frame and movably fixed to an edge of the base, wherein the at least one clamp is coupled to a track allowing the at least one clamp to be movable with the material on the base;
    controlling a loading mechanism to apply a desired load quantity on the material on the base to test the wrinkle resistance of the material; and
    sensing the movement of the at least one clamp in multiple directions.

8. The method of claim 7, wherein the loading mechanism comprises a pressure head to apply a constant load quantity to the material.

9. The method of claim 7, wherein the loading mechanism rotates while applying a desired load quantity on the material on the base.

10. The method of claim 7, wherein the step of controlling a loading mechanism further comprises applying a desired load quantity within a predetermined target value.

11. The method of claim 10, wherein the predetermined target value is from about 1 kilograms (kg) to about 10 kg.

12. The method of claim 7, wherein the at least one clamp is coupled to a track allowing the clamp to be movable with the material on the base.

13. The method of claim 7 further comprising calculating the average distance moved by the at least one clamp.

14. The method of claim 7 further comprising controlling the at least one clamp to hold the material at a constant tension via at least one strain gauge.

* * * * *